United States Patent [19]

Long, Jr.

[11] Patent Number: 4,865,836

[45] Date of Patent: Sep. 12, 1989

[54] BROMINATED PERFLUOROCARBON EMULSIONS FOR INTERNAL ANIMAL USE FOR CONTRAST ENHANCEMENT AND OXYGEN TRANSPORT

[75] Inventor: David M. Long, Jr., El Cajon, Calif.

[73] Assignee: Fluoromed Pharmaceutical, Inc., San Diego, Calif.

[21] Appl. No.: 818,690

[22] Filed: Jan. 14, 1986

[51] Int. Cl.$^4$ .................... A61K 49/04; A61K 47/00
[52] U.S. Cl. ........................................ 424/5; 514/174; 514/182; 514/458; 514/772; 514/832
[58] Field of Search ...................... 514/832, 772; 424/5

[56] References Cited

U.S. PATENT DOCUMENTS

| | | | |
|---|---|---|---|
| 3,818,229 | 6/1974 | Long, Jr. | |
| 3,958,014 | 5/1976 | Watanabe et al. | 424/366 |
| 3,962,439 | 6/1976 | Yokoyama et al. | 514/832 |
| 3,975,512 | 8/1976 | Long | 424/5 |
| 4,073,879 | 2/1978 | Long, Jr. | 424/5 |
| 4,105,798 | 8/1979 | Moore et al. | 514/435 |
| 4,146,499 | 3/1979 | Rosano | 252/187 H |
| 4,343,797 | 8/1982 | Ecanow | 514/832 |
| 4,397,870 | 8/1983 | Sloviter | 424/325 |
| 4,423,077 | 12/1983 | Sloviter | 514/832 |
| 4,439,424 | 3/1984 | Ecanow | 514/832 |
| 4,450,841 | 5/1984 | Osterholm | |
| 4,497,829 | 2/1985 | Sloviter | 514/832 |
| 4,605,786 | 8/1986 | Yokoyama et al. | 514/832 |
| 4,613,708 | 9/1986 | Riess et al. | 514/832 |
| 4,640,833 | 2/1987 | Tamborski et al. | 514/832 |
| 4,654,337 | 3/1987 | Yokoyama et al. | 514/832 |

FOREIGN PATENT DOCUMENTS

| | | |
|---|---|---|
| WO8100 | 1/1981 | European Pat. Off. |
| 0091183 | 12/1983 | European Pat. Off. |
| 8711780 | 10/1986 | European Pat. Off. |
| 8730045 | 1/1987 | European Pat. Off. |
| 2515198 | 10/1981 | France |
| 8032829 | 8/1981 | Japan |
| 9046230 | 8/1982 | Japan |
| 9067229 | 8/1982 | Japan |
| 0166626 | 9/1984 | Japan |

OTHER PUBLICATIONS

Beisbharth, H. and T. Suyama, 5th Intl. Symp. on Perfluorochemical Blood Substitutes, Mainz: Mar. 1981.
Persico, D. et al., "A General Synthesis for Symmetrical Highly Branched Perfluoro Ethers: A New Class of ... etc", J. Org. Chem. 50: 5156-5169 (1985).
Sharts, C. and H. Reese, The Solubility of Oxygen in Aqueous Fluorocarbon Emulsions, J. Fluorine Chemistry 11: 637-641 (1978).
S. Davis, 2nd International Symposium on Clinical Nutrition Advances in Clinical Nutrition 19: 213-239, Bermuda: May 1982.
Yokoyama, K. et al., Preparation of Perfluorodecalin Emulsion, An Approach to the Red Cells Substitute, Fed. Proc. 34(6), 1478-1483 (1975).
Steiner, M. and J. Anastasi, J. Clinical Investigation 57: 732-737 (1976).
Pandolfe, W. D. and R. R. Kinney, "Recent Developments in the Understanding of Homogenization Parameters", Denver, Colorado, Aug. 29, 1983.
Microfluidization, Microfluidics Corporation, Newton, MA.
Chandonnet, S. et al., Preparation of Microemulsions by Microfluidization, Feb. 1985.
Korstvedt, H. et al., Microfluidization: For Making Fine Emulsions and Dispersions, Amer. Paint and Coatings Journal, Jan. 28, 1985.
Korstvedt, H. et al., Microfluidization, Drug and Cosmetic Industry, Nov. 1984.
Dispersions, Prepared Foods, Mar. 1985.
Allinger, H., Ultrasonic Disruption, American Laboratory, Oct. 1985.
Berlinger, S., Application of Ultrasonic Processors, Biotechnology Laboratory, Mar. 1984.
Gould, S. et al., Assessment of a 35% Fluorocarbon Emulsion, The Journal of Trauma 23(8): 720-724, 1983.
Police, A. M. et al., Critical Care Medicine 12(2):96-98, 1985.
Nunn, G. R. et al., Effect of Fluorocarbon Exchange Transfusion on Myocardial Infarction Size in Dogs, American J. of Cardiology 52:203-205, 1983.
Bose, B. et al., Brain Research 328:223-231, 1985.
Spears, J. et al., Circulation (Abstracts), 68 (Supp. III), No. 317, Oct. 1983.
Patel, M. et al., Survival and Histopathological Changes in Lungs of Hamsters Following Liquid Synthetic Breathing, Fed. Proceedings 29(5):1740-1745, 1970.
Itoth, Y. et al., Gan To Kagaku Ryoho, 11(4):864-872, 1984.
A Technical Bulletin, #67 of the Gaulin Corporation, Sep. 1982.
Peck, W. W. et al., Investigative Radiology, 19:129, 1984.
Dobben, G. et al., Experimental Studies with Radiopaque Fluorocarbon in the Subarchnoid Space, Neuroradiology, 6:17-19, 1973.
Brahme, F. et al., Investigative Radiology, 11(4):319-330, 1976.
Long, D. M. et al., Radiology, 105(2):323-332, 1972.

*Primary Examiner*—Frederick E. Waddell
*Attorney, Agent, or Firm*—Knobbe, Martens, Olson & Bear

[57] ABSTRACT

A brominated perfluorocarbon emulsion non-toxic for internal and intravenous use in animals including humans for use as an oxygen transport medium and as a tumor and other element contrast enhancement medium is stable with very small size characteristics for extended periods in excess of eighteen months and after sterilization, with a stabilizing component selected from the class comprising steroid hormones, tocopherols, cholesterols and their combinations. An anti-oxidizing component enhances delivery in oxygen transport.

22 Claims, No Drawings

BROMINATED PERFLUOROCARBON EMULSIONS FOR INTERNAL ANIMAL USE FOR CONTRAST ENHANCEMENT AND OXYGEN TRANSPORT

BACKGROUND OF THE INVENTION

1. Field of the Invention

The present invention relates to the art of non-toxic oxygen transport and contrast enhancement agents, and more particularly to stable emulsions capable of sterilization and suitable for internal and intravenous animal, including human, use where the emulsion is a brominated perfluorocarbon in the discontinuous phase in the presence of certain what are believed to be stabilizing agents.

2. Description of the Prior Art

Mono-brominated cyclic and acyclic perfluorocarbons in aqueous emulsions with a minor amount of an emulsifying agent have been known for medical applications involving animals, including humans, for both radiopacity and oxygen delivery. Oxygen is highly soluble in, for example, perfluoroctylbromides. See Long, U.S. letters Pat. No. 3,818,229; No. 3,975,512; and, No. 4,073,879. The present invention is directed toward improvements in the use of such bromofluorocarbons wherein the oxygen transport characteristics, as well as the storage characteristics of the emulsions are enhanced, while the toxicity is further minimized or decreased altogether.

In the past, efforts to use emulsified fluorocarbons as an oxygen transport or carrier, as in a blood substitute, have encountered certain difficulties. Purity, non-toxicity, chemical and biological inertness and excretability are necessary objectives. The emulsified fluorocarbon must be capable of sterilization, preferably by heat, have long-term size and function stability in the fluid or non-frozen state, be industrially feasible, persist for sufficiently long times in the blood stream when used intravascularly and be eliminated rapidly from the body. It has been conventionally believed that those fluorocarbons which have fast elimination times from the body do not form stable emulsions, and that those fluorocarbons which form stable emulsions are retained too long in the body. Non-brominated perfluorocarbons show a direct relationship between emulsion stability and molecular weight and an inverse relationship between molecular weight and excretion rates from the animal body. Both types of fluorocarbons are inadequate, and attempts to combine amounts of both types have merely combined the problems of each.

For intravenous use, it is considered important to have small particle size. However, long term storage for extended periods of time for a month and longer, of fluorocarbon blood substitutes, or "synthetic blood" has heretofore resulted in conglomeration of the fluorocarbon particles of the emulsion into larger particles, especially after heat sterilization. For a general discussion of the objectives and a review of the efforts and problems in achieving these objectives in fluorocarbon blood substitutes, see "Reassessment of Criteria for the Selection of Perfluoro Chemicals for Second-Generation Blood Substitutes: Analysis of Structure/Property Relationship" by Jean G. Riess, 8 *Artificial Organs*, 34–56 (1984).

Larger particle sizes are dangerous in intravenous use in that they tend to collect in the lung, spleen and some other organs, enlarging them and endangering their functioning. On the other hand, it is desired to have sufficient particle size in the fluorocarbon particles for them to collect in tumors and other areas when the fluorocarbons are used as a contrast enhancement medium. Larger particle sizes, also, are unobjectionable when used in other, non-venous systems in the body, such as, for example, the cerebrospinal fluid ventricles and cavities.

DESCRIPTION OF THE PREFERRED EMBODIMENTS

In brief, one aspect of the present invention comprises mono-brominated perfluorocarbon emulsions. The bromofluorocarbon emulsions found suitable for use as an oxygen transport medium comprise mono-brominated perfluorocarbons having a minor amount of an emulsifying agent and further comprising a compound believed to be useful in stabilizing the membrane of the bromofluorocarbon particle. The compound could be steroid hormones, cholesterol, tocopherols and mixtures thereof. A nine-alpha fluorinated corticosteroid in combination with cholesterol emulsified along with a phosphatidylcholine to particles of a perfluoroctylbromide having the formula $CF_3(CF_2)_6CF_2Br$ or $C_8F_{17}Br$, or of related brominated perfluorocarbon such as a perfluorohexylbromide ($C_6F_{13}Br$) or a perfluoroseptobromide ($C_7F_{15}Br$), together with a tocopherol as an anti-oxidant is preferred.

It has been found that particle size stability can be maintained with emulsions of from 20% weight per volume to 125% weight per volume of the bromofluorocarbon without undesirable viscosity. Herein in this specification, the expression "weight per volume" or "w/v" will be used and understood to mean the ratio of percentage weight per grams per 100 cubic centimeters or milliliters, or equivalent expressions or mathematical identities thereof. Emulsions with concentrations of from 20% to 100% weight per volume have a thixotropic viscosity profile less than that of whole human blood. Perfluoroctylbromide is excreted rapidly from the animal body, because of the lipotrophic nature of the brominated perfluorocarbon, it is believed. In any event and notwithstanding its high molecular weight and stability, mono-brominated perfluorocarbon has a relatively high excretion rate from the animal body.

In some applications where high bromide concentration, such as when the emulsion is to be used as a contrast enhancement medium, or where a high oxygen transport is needed in an intravascular system where large volume impact is to be minimized, the larger concentration emulsion is preferred. While it is not certain, it is considered that these suitable and stable high bromofluorocarbon concentration emulsions are possible because (1) of the relatively high molecular weight of the brominated perfluorocarbon, and (2) of the good bonding between the bromine and the phospholipid emulsifying agent discussed below.

The preferred emulsifying agent is a phospholipid, an anionic surfactant or a fluorinated surfactant. Suitable phospholipids include lecithin, such as phosphatidylcholine. Phospholipids are common and biologically accepted elements in the blood, and are not so readily phagocytosed by macrophages or other organisms in the animal body's fluids. The resultant emulsion thus is resistant to macrophage and other animal body organism attack.

Preferred anionic surfactants include polyoxyethylene-polyoxypropylene copolymers, such as Pluronic. Suitable fluorinated surfactants include XMO10 and XMO20.

The phospholipid emulsifying agent should be included in the range of from 2 to 14 grams weight per volume, with the preferred amount being 6 grams weight per volume for concentrations of 75% w/v bromofluorocarbon and 7 grams to 10 grams weight per volume for concentrations of 100% bromofluorocarbon. The phospholipid leci thin contains both hydrophilic and hydrophobic or lipophilic characteristics and is thus a suitable emulsifying agent for the perfluorocarbon particle.

According to one embodiment of the present invention, an additional compound is made part of the particle in emulsion. The additional component is believed to be effectual in making the discontinuous particle membrane more compatible and stronger with respect to the continuous, aqueous phase of the emulsion. The additional component could be a tocopherol, a steroid hormone, a cholesterol or, preferably, a combination of these three components. Suitable steroid hormones include fluorinated corticosteroids, fluorinated androgens and non-fluorinated hormones, such as progesterones and estrogens. The preferred steroid is one that is fluorinated in either the nine-alpha or the six-alpha positions, such as, for examples, nine-alpha-fluoro-16-alpha-methylprednisolone, nine-alpha-fluoro-16-betamethyl-prednisolone, nine-alpha-fluoro-16-alpha-hydroxyprednisolone and six-alpha-fluoro-16-alpha-methylprednisolone, or combinations of these corticosteroids. While the actual reaction or membrane structure that takes place is not known, it is believed that the affinity of the fluorine in the fluorinated corticosteriod with the fluorine in the bromofluorocarbon creates a more compatible and reliable bond between the steroid and the perfluorocarbon particle to form a more stable membrane for the perfluorocarbon particle in the discontinuous phase of the emulsion.

Red blood cells have cholesterol on their cell membranes removed to be joined with the membrane of the fluorocarbon particles, which form close union with and have an affinity for the fluorocarbon particles, it is believed. Fluorocarbon particles having a significant coating of the cholesterols will deter the removal of cholesterol from the red blood cells, it is believed. Somewhat similarly, tocopherols and steroid horomes enhance the stability of the membrane of the perfluorocarbon particle.

The steroids nine-alpha-fluoro-16-alpha-methyl-prednisolone and nine-alpha-fluoro-16-beta-methylprednisolone, and other additional components if any are combined with them, should be included in an amount from 0.5 mg. to 5 mg. (or 0.0001 to 0.005 percent) weight per volume (w/v) in the emulsion. Six times this quantity of the steroid nine-alpha-fluoro-16-alpha-hydroxyprednisolene and combined additional components may be used. Three times the range given may be used if the steroid six-alpha-fluoro-16-alpha-methylprednisolone and any additional component is used. The actual amount of the additional component or components is a function of the contemplated dose, and of the amount of bromofluorocarbon in the ultimate emulsion. In this specification, the term "biocompatible" is used to denote that amount or quantity which is compatible with, and above which toxicity results in the biological system into which the emulsion containing the biocompatible element is to be introduced. There are biocompatible limits for steroids and cholesterols. It may be that additional amounts or quantities of the steroids and cholesterols are biocompatible, but the range given has been found to be sufficient to achieve the particle size stability and efficacious compatibility with red blood cells and other components in the blood stream and other fluid systems of the animal body.

Other nutrients may be added to the ultimate emulsion, such as, for example, glucose, amino acids, proteins and lipids.

Oxygen is highly soluble in the perfluorocarbons and in particular the mono-brominated perfluorocarbons of the present invention. In using the present invention as an oxygen transport medium, it is important to retain the oxygen as part of the perfluorocarbon particle for a reasonable period of time in order to transport the oxygen throughout the vascular system or to increase intravascular dwell time. It is found that the tocopherols such as the alpha-tocopherol, and water soluble analogs of tocopherols are suitable anti-oxidants which will retard rapid oxidation. Other anti-oxidants that are useful are ascorbic acid and calcium ascorbate. Adding anti-oxidants to the emulsion in an amount of from 0.01% to 0.5% weight per volume has been found useful to retard oxidation of the lipid emulsifier which diminishes the stability of the emulsion. Anti-oxidants also quench free radicals such as superoxide or hydroxyl atoms which are harmful to biological systems.

For contrast enhancement use and for oxygen transport use internally in an animal, including humans in other than the blood stream, such as in the cerebrospinal system, in the eye and in the tracheobronchial passages, for examples, larger particle sizes can be tolerated, and indeed may even be preferred. Such larger particle sizes may provide for a more even distribution of the gas, such as oxygen. Particle sizes of less than 400 nanometers diameter for the substantial portion, on the order of 95% of the particles, with a median particle diameter of less than 150 nanometers is to be preferred, however, for use in the blood stream. Effective oxygen unloading or de-oxygenation occurs in the blood stream primarily in the capillaries, and the small bromofluorocarbon particle size is advantageous in getting the oxygen to these capillaries. For these sizes for use in the blood stream, and even for the emulsions to be used in non-vascular systems, it is highly important to maintain particle size characteristics stable over extended periods of time, at least more than one month and of the order of eighteen months and more.

I have achieved particle sizes of perfluorocarbon emulsions in commercially usable quantities having very small sizes or diameters on the order of hundreds of nanometers using conventional particle fractionalization methods, such as the homogenization techniques using the Gaulin mixer. Bromo-perfluorocarbon emulsions made with such a technique appear to be suitably stable where the concentration of the bromo-perfluorocarbon is relatively small, on the order of less than 50% weight per volume. Attempts using the Gaulin mixer to prepare commercially usable quantities of bromo-perfluorocarbon emulsions having w/v concentrations of 50%, 75% and more and having a median particle diameter size of less than 200 nanometers were unsuccessful. These higher concentration bromo-perfluorocarbon emulsions were observed to have a median particle diameter size of more than 200 nanometers.

Long term, extended period of time small particle size stability of higher concentrations of mono-brominated perfluorocarbon emulsion in an aqueous phase with a phospholipid emulsifying agent has been found when the emulsion is formed or generated using a plural flow impingement apparatus. The aqueous phase was buffered with sodium mono-phosphate and sodium di-phosphate in such an amount to give a resultant emulsion pH of between 6.8 and 7.2. The aqueous phase, further, was in a solution of glycerol to control the osmolarity of the resultant emulsion for use in the blood stream. This buffered, aqueous phase solution in glycerol is sometimes designated the vehicle.

The bromofluorocarbon was metered in a predetermined, measured rate into the vehicle or aqueous phase having the emulsifying agent mixed therein. The resulting mixture was placed into a flow path which was divided into a plurality of flow paths. The flows were redirected to impinge upon each other at velocities in excess of 1500 feet per second in sheets of interaction in a cavity under 4,000 pounds per square inch or more of pressure. The resulting bromofluorocarbon particles had a size characteristic of more than 95% smaller than 350 nanometers in diameter, with the median size diameter of less than 150 nanometers and, significantly, these size characteristics were maintained stable for up to sixteen months, and even after sterilization, such as by heat or by filtration.

The present invention can be further understood by reference to the following illustrative examples.

EXAMPLE I

Exchange transfusions were performed in female rats weighing 180 to 220 grams. The rats were anesthetized and polyethylene catheters were inserted into the left or right jugular vein and carotid artery. After recovery from the anesthesia, the rats were placed into an atmosphere enriched with 50% to 60% oxygen. Blood was removed through the carotid artery cather and a comparable amount of the brominated perfluorocarbon emulsion comprising 25% w/v of perfluoroctylbromide, 4% w/v of lecithin, 0.04% w/v of L-alpha-tocopherol, 2.21% w/v of glycerol, 0.012% w/v of sodium di-phosphate, 0.057% w/v of sodium mono-phosphate and the aqueous phase. The transfusion was continued until the red blood cell count of the rat was reduced to 50% of the baseline value. The rats were kept in the oxygen enriched atmosphere for twenty-four hours, after which they were removed to the ordinary atmosphere. All rats survived for more than one month.

EXAMPLE II

The experiment of Example I was repeated, except that the brominated perfluorocarbon emulsion comprised 50% w/v of perfluoroctybromide. All other parameters were the same. All rats survived for more than one month.

EXAMPLE III

Balb C mice were administered intravenously the brominated perfluorocarbon emulsion at doses of 45 grams per kilogram of body weight, and were administered intraperitoneally the brominated perfluorocarbon emulsion in doses of 100 grams per kilogram of body weight. The emulsion comprised 100% w/v of perfluoroctylbromide, 9.1% w/v of lecithin, 0.02% w/v of 6-alpha-fluoro-16-alpha-methylprednisolone, 0.2%% w/v of alpha-tocopherol, 1.0% w/v of glycerol, 0.012% w/v of soduim di-phosphate, 0.057% w/v of sodium mono-phosphate and the aqueous phase. After seven days, the liver and spleen were enlarged, but the peritoneal cavity showed no signs of inflammation, and the lungs were normal and filled with oxygen. There were no signs of hemorrhage or pulmonary congestion, or of inflammation of the tissues of the abdominal wall.

EXAMPLE IV

A mono-brominated perfluorocarbon emulsion comprising 100% w/v of perfluoroctylbromide, 9.1% w/v of lecithin, 0.02% w/v of 6-alpha-fluoro-16-alpha-methylprednisolone, 0.2% w/v of alpha-tocopherol, 1.0% w/v of glycerol, 0.012% w/v of soduim di-phosphate, 0.057% w/v of sodium mono-phosphate and the aqueous phase was prepared by first preparing the vehicle of the continuous or aqueous phase by blending in the lecithin, the 6-alpha-fluoro-16-alpha-methylprednisolone, the alpha-tocopherol, the glycerol, the soduim di-phosphate, sodium mono-phosphate. The perfluoroctylbromide was added in a measured rate into the vehicle while mixing. The resulting emulsion at 10 degrees C. was passed through a microfluidizing apparatus in the method described herein where a plurality of flows of the emulsion were impinged upon each other at velocities in excess of 1500 feet per second, for fifteen passes. The particle size distribution was analyzed in a Nicomp submicron particle sizer manufactured by Pacific Scientific Co. of Anaheim, Aalif. This analyzer determines relative quantities of various sized particles by a method of dynamic light scattering. Results according to the following Table I were given, where the first column represents the diameter of the particles in nanometers, and the second column represents a quantitative value of the relative quantity of the particles detected at the corresponding particle size:

TABLE I

| SIZE nanometers | |
|---|---|
| 84.2 | ***************************************************** |
| 85.7 | ***************************************************** |
| 87.2 | ************************************************** |
| 88.8 | |
| 90.5 | |
| 92.3 | |
| 94.1 | |
| 96.0 | |
| 97.9 | |
| 100.0 | |
| 102.1 | |
| 104.3 | |
| 106.6 | |
| 109.0 | |
| 111.6 | |
| 114.2 | |
| 117.0 | |
| 120.0 | |
| 123.0 | |
| 126.3 | |
| 129.7 | |
| 133.3 | |
| 137.1 | |
| 141.1 | |
| 145.4 | |
| 150.0 | |
| 154.8 | |
| 160.0 | |
| 165.5 | |
| 171.4 | |
| 177.7 | |
| 184.6 | |
| 192.0 | |
| 200.0 | *** |
| 208.6 | ******* |
| 218.1 | *********** |

TABLE I-continued

| SIZE nanometers | |
|---|---|
| 228.5 | ************** |
| 240.0 | ********* |
| 252.6 | ***** |
| 266.6 | |
| 282.3 | |
| 300.0 | |
| 320.0 | |
| 342.8 | |
| 369.2 | |
| 400.0 | |
| 436.3 | |
| 480.0 | |
| 533.3 | |
| 600.0 | |
| 685.7 | |
| 800.0 | |
| 960.0 | |
| 1200.0 | |
| 1600.0 | |
| 2400.0 | |
| 4800.0 | |

The emulsion was then sterilized at 90 degrees C. for fifteen minutes. After sterilization, the Nicomp emulsion particle size characteristics were measured on the Nicomp particle sizer. The results, given in the Table II below where the columns represent the same characteristics as set forth for Table I, showed no significant particle size characteristic deterioration or change:

TABLE II

NICOMP Distribution Analysis (Solid Particles)

| SIZE nanometers | |
|---|---|
| 84.2 | ***************************************************** |
| 85.7 | ************************************************** |
| 87.2 | ************************************************ |
| 88.8 | |
| 90.5 | |
| 92.3 | |
| 94.1 | |
| 96.0 | |
| 97.9 | |
| 100.0 | |
| 102.1 | |
| 104.3 | |
| 106.6 | |
| 109.0 | |
| 111.6 | |
| 114.2 | |
| 117.0 | |
| 120.0 | |
| 123.0 | |
| 126.3 | |
| 129.7 | |
| 133.3 | |
| 137.1 | |
| 141.1 | |
| 145.4 | |
| 150.0 | |
| 154.8 | |
| 160.0 | |
| 165.5 | |
| 171.4 | |
| 177.7 | |
| 184.6 | |
| 192.0 | |
| 200.0 | |
| 208.6 | **** |
| 218.1 | ******** |
| 228.5 | *************** |
| 240.0 | ********** |
| 252.6 | ****** |
| 266.6 | * |
| 282.3 | |
| 300.0 | |
| 320.0 | |
| 342.8 | |

TABLE II-continued

NICOMP Distribution Analysis (Solid Particles)

| SIZE nanometers | |
|---|---|
| 369.2 | |
| 400.0 | |
| 436.3 | |
| 480.0 | |
| 533.3 | |
| 600.0 | |
| 685.7 | |
| 800.0 | |
| 960.0 | |
| 1200.0 | |
| 1600.0 | |
| 2400.0 | |
| 4800.0 | |

EXAMPLE V

An emulsion particle size stability over an extended period of time was studied by analyzing the particle size distribution in a Nicomp sub-micron particle sizer identified above for the Example IV. The brominated perfluorocarbon emulsion first was made by the methods described above and comprised 25% w/v of perfluoroctylbromide, 4% w/v of lecithin, 0.04% w/v of L-alphatocopherol, 2.21% w/v of glycerol, 0.012% w/v of sodium di-phosphate, 0.057% w/v of sodium mono-phosphate and the aqueous phase. The emulsion was analyzed shortly after formulation, and the relative quantities of the emulsion's particle sizes is given in the following Table III, where the scale and columns represent the same characteristics as set forth for the tables in Example IV:

TABLE III

| SIZE nanometers | |
|---|---|
| 3599.9 | |
| 1799.9 | |
| 1200.0 | |
| 900.0 | |
| 719.9 | |
| 600.0 | |
| 514.2 | |
| 450.0 | |
| 400.0 | |
| 359.9 | *** |
| 327.2 | ******** |
| 300.0 | **************** |
| 276.9 | ****************** |
| 257.1 | ************** |
| 240.0 | ***** |
| 225.0 | |
| 211.7 | |
| 200.0 | |
| 189.4 | |
| 179.9 | |
| 171.4 | |
| 163.6 | |
| 156.5 | |
| 150.0 | |
| 143.9 | |
| 138.4 | |
| 133.3 | |
| 128.5 | |
| 124.1 | |
| 120.0 | |
| 116.1 | |
| 112.5 | |
| 109.0 | |
| 105.8 | |
| 102.8 | |
| 100.0 | |
| 97.2 | |
| 94.7 | |
| 92.3 | |
| 90.0 | |

TABLE III-continued

| SIZE nanometers | |
|---|---|
| 87.8 | |
| 85.7 | * |
| 83.7 | ******************* |
| 81.8 | ************************************ |
| 80.0 | ****************************************************** |
| 78.2 | ************************************** |
| 76.5 | ******************* |
| 75.0 | |
| 73.4 | |
| 71.9 | |
| 70.5 | |
| 69.2 | |
| 67.9 | |
| 66.6 | |
| 65.4 | |
| 64.2 | |
| 63.1 | |

The emulsion was stored at 4 degrees C., although for various interruptions during the time of storage the temperature was changed, frequently being very substantially higher. A second and substantially identical analysis was made using the Nicomp particle sizer as described above some fifteen months and 22 days after the analysis given in Table III. The results of this second analysis is given in the following Table IV, where the scale and columns represent the same characteristics as set forth for the tables in Example IV:

TABLE IV

NICOMP Distribution Analysis (Solid Particles)

| SIZE nanometers | |
|---|---|
| 21.0 | |
| 21.4 | |
| 21.8 | |
| 22.2 | |
| 22.6 | |
| 23.0 | |
| 23.5 | |
| 24.0 | ************** |
| 24.4 | ************************ |
| 25.0 | ************** |
| 25.5 | ******************************************************* |
| 26.0 | ************************************************ |
| 26.6 | ****************************************************** |
| 27.2 | |
| 27.9 | |
| 28.5 | |
| 29.2 | |
| 30.0 | |
| 30.7 | |
| 31.5 | |
| 32.4 | |
| 33.3 | |
| 34.2 | |
| 35.2 | |
| 36.3 | |
| 37.5 | |
| 38.7 | |
| 40.0 | |
| 41.3 | |
| 42.8 | |
| 44.4 | |
| 46.1 | |
| 48.0 | |
| 50.0 | |
| 52.1 | |
| 54.5 | |
| 57.1 | |
| 60.0 | |
| 63.1 | |
| 66.6 | |
| 70.5 | |
| 75.0 | |
| 80.0 | |
| 85.7 | ************ |

TABLE IV-continued

NICOMP Distribution Analysis (Solid Particles)

| SIZE nanometers | |
|---|---|
| 92.3 | ********** |
| 100.0 | ********* |
| 109.0 | * |
| 120.0 | *** |
| 133.3 | *** |
| 150.0 | |
| 171.4 | |
| 200.0 | ** |
| 240.0 | ******* |
| 300.0 | ******* |
| 400.0 | ****** |
| 600.0 | **** |
| 1200.0 | ** |

The foregoing detailed description of my invention and of preferred embodiments, as to products, compositions and processes, is illustrative of specific embodiments only. It is to be understood, however, that additional embodiments may be perceived by those skilled in the art. The embodiments described herein, together with those additional embodiments, are considered to be within the scope of the present invention.

I claim:

1. A process for preparing a brominated perfluorocarbon emulsion capable of carrying oxygen to animal tissues having size stability characteristics for an extended period of time and resistant to attack by animal organisms in animal body fluids, comprising the steps of:
   a. dispersing purified phospholipid emulsifier in a buffered aqueous solution containing an osmotic agent, and a biocompatible amount of a compound selected from the group consisting of sterols, tocopherols and combinations thereof;
   b. gradually mixing into said dispersed emulsifier and solution from about 55% to about 125% weight per volume of brominated perfluorocarbon; and,
   c. directing said mixture through a emulsification apparatus having fluid velocities of at least 1500 feet per second under such high shear conditions as to form a stable, heat-sterilizable emulsion, wherein the amount of emulsifier in said emulsion is an effective amount and the amount of osmotic agent and the buffer are effective to approximate physiological biocompatible osmolarity and pH.

2. A process for preparing a brominated perfluorocarbon emulsion capable of carrying oxygen to animal tissues having size stability characteristics for an extended period of time, comprising the steps of:
   a. dispersing purified emulsifier in a buffered aqueous solution of an osmotic agent;
   b. mixing from about 55% to 125% weight per volume of brominated perfluorocarbon into said dispersion of emulsifier and solution; and,
   c. passing the resulting mixture through an emulsifying apparatus generating such high shear conditions as to form a stable, heat-sterilizable emulsion, wherein the amounts of buffer and osmotic agent in said emulsion are effective to approximate physiological pH and osmolarity.

3. The process of claim 2, wherein said passing step further comprises passing the resulting mixture through said emulsifying apparatus a plurality of times in a plurality of flows in separate flow paths and redirecting said plurality of flows into each other at least 4,000 pounds per square inch of pressure.

4. The process of claim 2 wherein in said passing step, said mixture is flowing at velocities in excess of 1500 feet per second.

5. A process for preparing a fluorocarbon emulsion capable of carrying oxygen to animal tissues, said emulsion having substantial particle size stability characteristics for an extended period of time and through heat sterilization, comprising the steps of:
   a. mixing an effective amount of an emulsifier in an aqueous phase;
   b. mixing of from about 55% to 125% weight per volume of a non-toxic fluorocarbon into said mixture of emulsifier and aqueous phase; and
   c. passing the fluorocarbon-containing mixture through a mechanical emulsifying apparatus having a flow path, in which said mixture is subjected to sufficiently high shear rates to form a stable, heat sterilizable emulsion.

6. The process of claim 5 wherein said passing step is repeated.

7. The process of claim 6 wherein said passing step is repeated at least four times.

8. The process of claim 5 wherein in said passing step, said flow is maintained at approximately 1500 feet per second velocity.

9. A process for preparing a fluorocarbon emulsion having particle size stability characteristics for an extended period of time, comprising the steps of:
   a. mixing an effective amount of emulsifier and from about 55% weight per volume to 125% weight per volume of a biocompatible fluorocarbon into an aqueous phase to form a mixture; and,
   b. placing said mixture in an emulsification apparatus and pressurizing said mixture at a pressure of at least 4000 pounds per square inch to force said mixture through at least one high shear emulsification flow path at a velocity of at least 1500 feet per second.

10. The process of claim 9 wherein in said pressurizing step, said mixture is forced into a plurality of flow paths which direct the mixture flows to impinge against each other in an impingement cavity.

11. The process of claim 9 wherein said mixing step, the fluorocarbon is mixed into said aqueous phase after said emulsifier is mixed into said aqueous phase.

12. The process of claim 11 wherein said fluorocarbon is mixed into said aqueous phase in said at least one flow path.

13. The process of claim 11 wherein in said mixing step, a buffering agent is mixed into said aqueous phase.

14. The process of claim 11 wherein in said mixing step, an osmotic agent is mixed into said aqueous phase.

15. The process of claim 9 wherein said fluorocarbon is a brominated fluorocarbon.

16. The process of claim 5, wherein said fluorocarbon-containing mixture is subjected to a pressure of at least 4000 pounds per square inch in said emulsifying apparatus.

17. The process of claim 5, wherein said fluorocarbon-containing mixture is subjected to flow rates of at least 1500 feet per second in said emulsifying apparatus.

18. A process for preparing a fluorocarbon emulsion capable of carrying oxygen to animal tissues, said emulsion having substantial particle size stability characteristics for an extended period of time though heat sterilization, comprising the steps of:
   combining an aqueous phase with an effective amount of an emulsifier and from about 50% to about 125% weight per volume of a fluorocarbon to form a mixture; and
   passing the fluorocarbon-containing mixture through a mechanical emulsification apparatus in which said mixture is subjected to sufficiently high flow rates and pressures to form a stable, heat sterilizable emulsion.

19. The process of claim 18, wherein said fluorocarbon is brominated.

20. The process of claim 18, wherein said mixture is subjected to a pressure of at least 4000 pounds per square inch in said emulsifying apparatus.

21. The process of claim 18, wherein said mixture is subjected to flow rates of at least 1500 feet per second.

22. The process of claim 18, wherein said mixture contains from about 80% to about 125% weight per volume of said fluorocarbon.

* * * * *